US006589217B2

United States Patent
Schachar

(10) Patent No.: US 6,589,217 B2
(45) Date of Patent: *Jul. 8, 2003

(54) DEVICE FOR THE TREATMENT OF MACULAR DEGENERATION AND OTHER EYE DISORDERS

(75) Inventor: Ronald A. Schachar, Dallas, TX (US)

(73) Assignee: RAS Holding Corp, Dallas, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/996,159

(22) Filed: Nov. 26, 2001

(65) Prior Publication Data

US 2002/0052652 A1 May 2, 2002

Related U.S. Application Data

(63) Continuation of application No. 09/711,819, filed on Nov. 13, 2000, now Pat. No. 6,322,545, which is a continuation of application No. 09/185,155, filed on Nov. 3, 1998, now Pat. No. 6,146,366.

(51) Int. Cl.[7] ............................................. A61M 35/00
(52) U.S. Cl. ........................................................ 604/294
(58) Field of Search ................................. 351/200; 623/4, 623/1, 5.11, 6.11, 6.63; 514/277; 604/289, 294

(56) References Cited

U.S. PATENT DOCUMENTS

| 4,957,506 A | * | 9/1990 | Mercier ..................... 623/6.35 |
| 5,558,630 A | * | 9/1996 | Fisher ......................... 623/905 |
| 5,824,685 A | * | 10/1998 | Campochiaro et al. ..... 514/277 |

* cited by examiner

Primary Examiner—George Manuel

(57) ABSTRACT

Introduced is a device that may be used to treat the effects of macular degeneration and other eye disorders by increasing the optical effect of the retinal surface of the eye. This may be accomplished using a device whose body has a shape prescribed to increase the depth of the fovea and, in the process, make the sides of the clivus more convex, thereby utilizing the varying optical properties of the retinal area. A suitable association of this device with the eye will cause an image beam traveling from the lens through the vitreous humor to magnify and impinge an image perception area encompassing the macula. According to one advantageous embodiment, the device includes a body adapted for association with the eye to manipulate the retina of the eye to effectively augment the photoreceptor cells proximate the macula of the eye. The body of the device may be that of a band, a segment, a partial band, a plate, or, for that matter, any shape suitably adapted to perform the functions described herein to treat the effects of macular degeneration as well as other eye disorders.

18 Claims, 6 Drawing Sheets

DEVICE FOR THE TREATMENT OF MACULAR DEGENERATION AND OTHER EYE DISORDERS

This application is a continuation of prior U.S. application Ser. No. 09/711,819 filed on Nov. 13, 2000, now U.S. Pat. No. 6,322,545, which is a continuation of prior U.S. application Ser. No. 09/185,155 filed on Nov. 3, 1998 now U.S. Pat. No. 6,146,366.

CROSS REFERENCE TO RELATED PATENT DOCUMENTS

The present disclosure is related to the inventions disclosed in the following United States patent applications and issued United States patents:

(1) U.S. patent application Ser. No. 08/463,749 entitled "TREATMENT OF PRESBYOPIA AND OTHER EYE DISORDERS" and filed Jun. 5, 1995;

(2) U.S. patent application Ser. No. 08/946,975 entitled "SCLERAL PROSTHESIS FOR TREATMENT OF PRESBYOPIA AND OTHER EYE DISORDERS" and filed Oct. 8, 1997;

(3) U.S. patent application Ser. No. 09/032,830 entitled "SEGMENTED SCLERAL BAND FOR TREATMENT OF PRESBYOPIA AND OTHER EYE DISORDERS" and filed Mar. 2, 1998;

(4) U.S. patent application Ser. No. 09/061,168 entitled. "SCLERAL PROSTHESIS FOR TREATMENT OF PRESBYOPIA AND OTHER EYE DISORDERS" and filed Apr. 16, 1998;

(5) U.S. Pat. No. 5,465,737 entitled "TREATMENT OF PRESBYOPIA AND OTHER EYE DISORDERS" and issued on Nov. 14, 1995;

(6) U.S. Pat. No. 5,489,299 entitled "TREATMENT OF PRESBYOPIA AND OTHER EYE DISORDERS" and issued on Feb. 6, 1996;

(7) U.S. Pat. No. 5,503,165 entitled "TREATMENT OF PRESBYOPIA AND OTHER EYE DISORDERS" and issued on Apr. 2, 1996;

(8) U.S. Pat. No. 5,529,076 entitled "TREATMENT OF PRESBYOPIA AND OTHER EYE DISORDERS" and issued on Jun. 25, 1996;

(9) U.S. Pat. No. 5,354,331 entitled "TREATMENT OF PRESBYOPIA AND OTHER EYE DISORDERS" and issued on Oct. 11, 1994; and

(10) U.S. Pat. No. 5,722,952 entitled "TREATMENT OF PRESBYOPIA AND OTHER EYE DISORDERS" and issued on Mar. 3, 1998;

which are commonly owned by the assignee of the present invention. The disclosures of these related United States patent applications and issued United States patents (collectively referred to hereafter as the "Presbyopia and Related Eye Disorder Patent Documents") are incorporated herein by reference for all purposes as if fully set forth herein.

TECHNICAL FIELD OF THE INVENTION

The present invention is generally related to the treatment of eye disorders and, more particularly, to device for the treatment of macular degeneration.

BACKGROUND OF THE INVENTION

Macular degeneration is a degenerative (age related) process that involves a highly specialized central part of the retina of the eye known as the macula, which is responsible for detailed central vision tasks such as reading, television viewing, sewing, etc. The various risk factors that may play a role in the cause of macular degeneration are being acutely studied—heredity, nutritional deficiencies, arteriosclerosis and hypertension, smoking, exposure to ultraviolet light, etc., are all suspect but further research is necessary to clearly identify the most significant factors.

Signs and symptoms of macular degeneration are gradual blurring or distortion of central vision interfering with basic functions, such as reading and other like activities. It is not at all uncommon to experience some loss of central visual function as a natural consequence of aging, although many individuals suffer more significant and even drastic loss of central vision.

In many early cases, vision may not be noticeably affected and the condition is discovered during a routine medical eye examination as there is a typical appearance to the macula which alerts the ophthalmologist to the problem. Tiny yellowish deposits of degenerative material are often noticed in the macular area as well as alterations in the normal structure and pigmentation of the macula. Glasses will not correct the poor vision caused by macular degeneration.

While some people experience only minor inconvenience from mascular degeneration and are able to compensate and lead normal lives, many others with more severe forms of macular degeneration may be incapacitated. Conventional treatment, including surgical procedures as well as therapeutic treatments, such as those employing systemic injection of a drug candidate, have had mixed results, and, in certain instances, have caused deleterious side effects. A need therefore exists for a treatment that reduces or limits the effects of macular degeneration.

SUMMARY OF THE INVENTION

To address the above-discussed deficiencies of the prior art, it is a primary object of the present invention to introduce a device that may be used through a surgical process to treat the effects of certain eye disorders, particularly macular degeneration. As introduced hereinabove, symptoms of macular degeneration include gradual blurring or distortion of central vision functions. Typically, tiny yellowish deposits of degenerative material called "drusen" appear in the macular area (or central retina), as well as alterations in the normal structure and pigmentation of the macula. Ultimately the macula area is destroyed.

In accordance with the principles of the present invention, introduced is a device that treats the effects of macular degeneration and other eye disorders by manipulating the optical effect of the retinal surface of the eye. According to one advantageous embodiment, this is accomplished using a device comprising a body that may be employed to increase the depth of the fovea and, in the process, to make the sides of the clivus more convex, thereby utilizing the varying optical properties of the retinal area to increase the optical effect of the same. In short, a suitable association of this device with the eye will cause an image beam traveling from the lens of the eye through the vitreous humor to magnify and impinge an image perception area that is relatively larger than the macula and preferably encompasses the same.

According to one advantageous embodiment, the device includes a body adapted for association with the eye, having a shape prescribed to manipulate the retina of the eye to effectively augment the photoreceptor cells proximate the macula. The prescribed shape of the body of the device is that of a band, a segment, a partial band, a plate, or, for that matter, any shape suitably adapted to perform the functions described or referenced herein to treat the effects of macular degeneration as well as other eye disorders. In point of fact, such body may likewise have any suitable geometric dimension and physical shape, including circular, round, rectangular, triangular, quadrilateral, conical, or other like form, or suitable combination of two or more of the same.

In a related embodiment, the device is comprised of a plurality of segments, each having a body with a prescribed shape that enables the segments to cooperatively manipulate the retina of the eye. Again, this manipulation augments the photoreceptor cells proximate the macula of the eye to form an increased image perception area that preferably encompasses the macula. According to a preferred embodiment, two or more segments may suitably be in physical association with one another, and, in alternate or related embodiments, two or more cooperating segments may not be physically associated. Nevertheless, such segments may form any one or more of a band, a combined segment, a partial band, a plate, or, again, any other shape suitably adapted to perform the functions described herein.

In short, a primary aspect of the device embodiments introduced here, and described in greater detail below, is their common capability to manipulate the optical effect of the retinal surface of the eye to treat certain eye disorders. This manipulation may directly, or indirectly, (i) increase the depth of the fovea; (ii) make the sides of the clivus more convex to more fully utilize the varying optical properties of the retinal area; (iii) augment the photoreceptor cells proximate the macula of the eye to form an increased image perception area; (iv) alter the effective focal distance between the lens and the retinal area; or (v) some combination of two or more of the same.

The foregoing SUMMARY OF THE INVENTION outlines, rather broadly, some advantageous features of various embodiments of the present invention so that those of ordinary skill in the art may better understand the DETAILED DESCRIPTION that follows. Additional features of the invention will be described hereafter that form the subject matter of the CLAIMS OF THE INVENTION. Those of ordinary skill in the art should appreciate that they can readily use the disclosed conception and specific embodiments as a basis for designing or modifying other structures for carrying out the same purposes of the present invention. Those of ordinary skill in the art should also realize that such equivalent constructions do not depart from the spirit and scope of the present invention in its broadest form.

Lastly, before undertaking the BRIEF DESCRIPTION OF THE DRAWINGS and the DETAILED DESCRIPTION, it may be advantageous to set forth several definitions (in addition to those already provided) for certain words and phrases used throughout this patent document, as follows: the terms "include" and "comprise," as well as derivatives thereof, mean inclusion without limitation, and may be used interchangeably; the term "or," is inclusive, meaning and/or; and the phrases "associated with" and "associated therewith," as well as derivatives thereof, may mean to include, be included within, interconnect with, contain, be contained within, connect to or with, couple to or with, be communicable with, cooperate with, interleave, be a property of, be bound to or with, have, have a property of, or the like. Definitions for certain words and phrases are provided throughout this patent document, and such definitions apply to prior, as well as future uses of such defined words and phrases.

BRIEF DESCRIPTION OF THE DRAWINGS

For a more complete understanding of the present invention, reference is now made to the following descriptions taken in conjunction with the accompanying drawings wherein like numbers represent like, or analogous, objects and, in which.

DETAILED DESCRIPTION

Figure 1A:
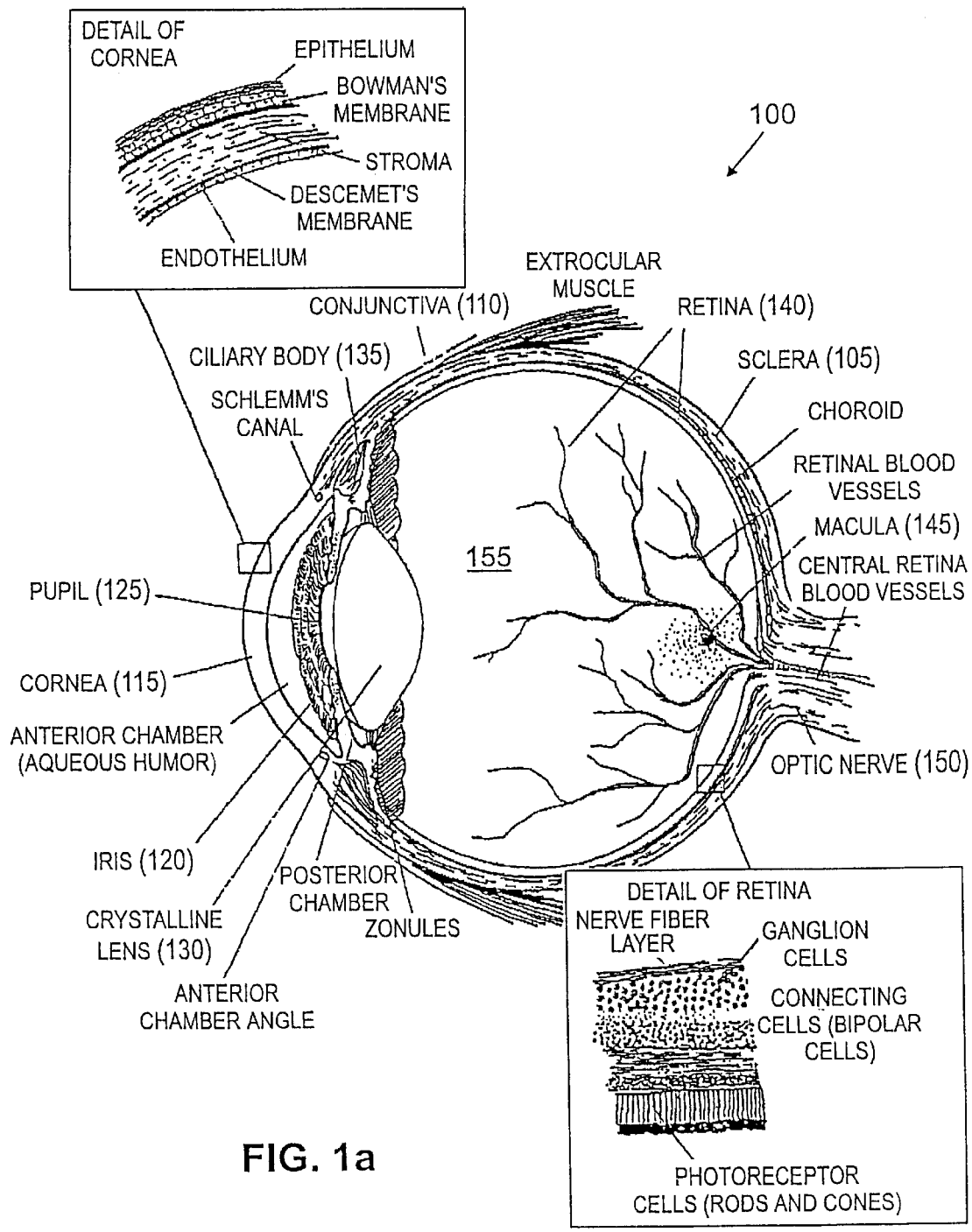
FIG. 1a illustrates a two-dimensional cross-sectional representation of an exemplary human eye.

Turning initially to FIG. 1a, illustrated is a two-dimensional cross-sectional representation of an exemplary human eye (generally designated 100) that details the basic anatomy of the same. For the purposes of illustrating the principles of the present invention, it is beneficial to describe the structure and function of a few parts of the eye 100, namely, the sclera 105, the conjunctiva 110, the cornea 115, the iris 120, the pupil 125, the crystalline lens 130, the ciliary body 135, the retina 140, the macula 145, the optic nerve 150, and the vitreous humor (generally designated 155).

The sclera 105 is the "white of the eye," which is a tough protective coat consisting of collagen and elastic tissues. The outermost layer of the sclera 105, called the episclera, is a thin filmy substance with numerous blood vessels. Scleral thickness varies at different points ranging from the thinnest portion (approximately 0.3 millimeters) near the muscle insertions to the thickest (approximately 1.0 to 1.3 millimeters) at the back of the eye. The conjunctiva 110 is the "skin" of the eye, which is a thin, filmy, transparent membrane covering the sclera 105. The conjunctiva 110 also lines the inner side of the eyelids and contains numerous blood vessels and some mucus and tear glands.

The cornea 115 is the clear, transparent "window" of the eye. The cornea 115 is approximately 12 millimeters in diameter and typically varies from a little more than one half millimeter in thickness centrally to a little less than a millimeter at the edges. The cornea 115 consists of five distinct layers (from front to back): epithelium, Bowman's membrane, stroma, Descemet's membrane, and endothelium. The cornea 115 contains numerous tiny nerve fibers, but no blood vessels. The iris 120 is the "colored part of the eye" (e.g., blue, brown, green, hazel, etc.). The iris 120 contains two major sets of muscles (for dilating and constricting the pupil) and numerous blood vessels and pigment cells and granules. The pupil 125 is the black "hole" or "space" in the center of the iris 120. The pupil 125 is not actually a structure or component of the eye 100, but an empty space, like an "open window."

The crystalline lens 130, along in cooperation with the cornea 115, provides for the focusing of light rays entering the eye 100. The lens 130, consisting of regularly oriented protein fibers surrounded by a clear capsule, is a biconvex disc suspended in place by the zonules connecting it to the ciliary body 135. The curvature of the lens 130 may be altered or changed, providing variable focus power to the eye 100. The ciliary body 135, along with the iris 120 and the choroid is considered part of the uveal tract or uvea of the eye. The ciliary body 135 contains numerous blood vessels and various muscles for focusing the eye 100, as well as the pigment cells and granules found in other parts of the uvea. The ciliary body 135 also serves as the point of attachment for the zonules or suspensory ligaments of the lens 130 and contains the cells that operate to secrete the aqueous humor found in the anterior and posterior chambers.

The retina 140 is the nerve cell layer of the eye 100 that functions much like the film in a camera. In short, the remainder of the eye 100 serves to focus light on to the retina 140 where photochemical reactions occur as part of the process of vision. The retina 140 is a thin, transparent tissue containing some 120 million separate rod cells (night vision) and 7 million cone cells (day and color vision) as well as millions of other structural supporting and interconnecting cells (collectively, the photoreceptor cells). The macula 145 is the sensitive, central, part of the retina that provides for sharp, detailed vision and contains the highest concentration of color-sensitive cone cells. The fovea (not shown) is the center of the macula 145. The retinal blood vessels course through the retinal substance and, along with the underlying choroid (the richly vascular, pigmented tissue situated between the retina 140 and the sclera 105), supply the necessary nutrients and oxygen for normal retinal function. These blood vessels are remote branches of the large carotid arteries in the neck and can become occluded by fragments of calcium and cholesterol which chip off from partially blocked carotid arteries and flow into the eye 100.

The optic nerve 150 is the main "trunk line," consisting of a million or so separate nerve fibers, conducting nervous impulses from the retina 140 to the brain (not shown). The optic nerve 150 exits at the back of the eye 100 and joins with the optic nerve 150 of the fellow eye at the optic chiasm (not shown). The vitreous humor 155 is a gel-like fluid that occupies the large space bounded by the lens 130 and ciliary body 135 in front and the retina 140 and optic nerve 150 in the back of the eye 100. The vitreous humor 155 serves a cushioning and protective function for the eye 100 and is normally optically clear. The vitreous humor 155 consists of collagen, mucopolysaccharides and hyaluronic acid in a delicate balance.

Figure 1B:
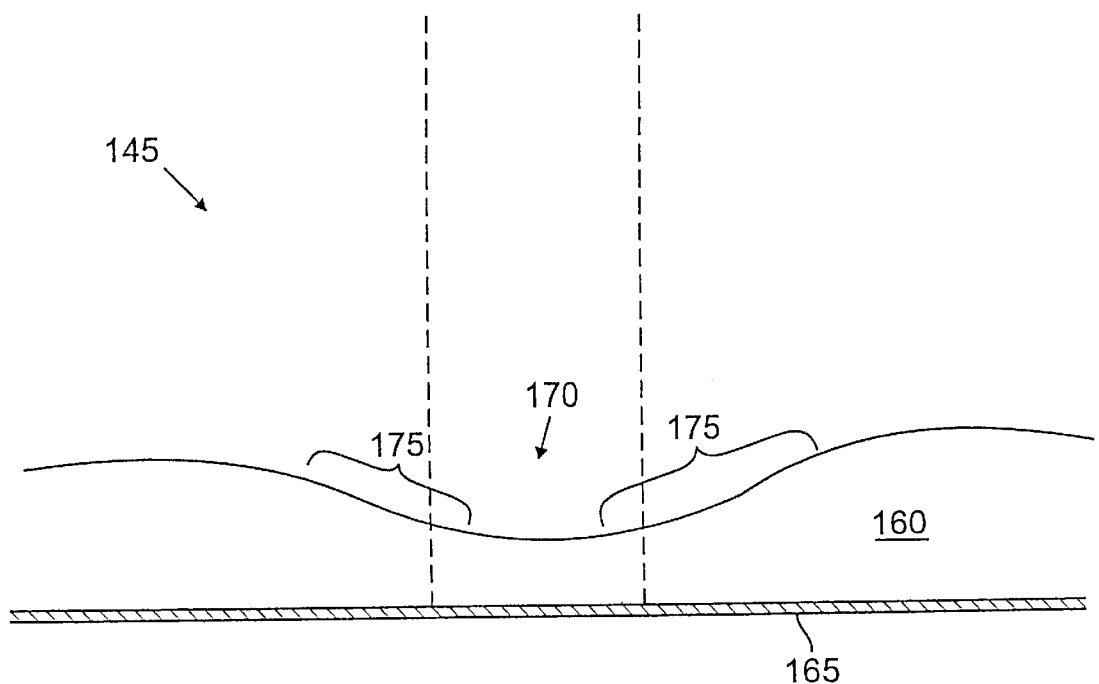
FIG. 1b illustrates a more detailed two-dimensional cross-sectional representation of the macula area of a human eye.

Turning next to FIG. 1*b*, illustrated is a more detailed two-dimensional cross-sectional representation of the macula area (generally designated 145) of a human eye, and, more particularly, the retinal tissue area 160 (which includes the nerve fiber layer, ganglion cells and the connecting cells of FIG. 1*a*), the photoreceptor cells 165, the fovea 170, and the clivus 175. The fovea 170 is a shallow rounded "pit" lying about 4 mm. to the temporal side of the optic disc and about 0.8 mm. below the horizontal meridian (noting that such distance varies, occasionally even between the two eyes). The depression is due to the practical disappearance of the inner layers of the retina, which is partly compensated by an increased thickness of the bacillary layer. The shape of the fovea 170 is that of a "shallow bowl" with a concave floor. The sides form a curving slope known as the clivus 175 descending from the foveal margin which, incidentally, is the thickest part of the retina. In the center of the "shallow bowl" is a slight dip, the foveola (or "little fovea," not shown) in the midst of which is a small central concavity, the umbo (or "navel," not shown). The photoreceptor cells 165 in the region of the floor of the fovea 170 are more cones and are closely packed, longer and more tenuous than in other regions of the retina. As the rods are eliminated and the cones are aggregated and slenderized, the threshold of stimulation of the area tends to rise.

Figure 2:
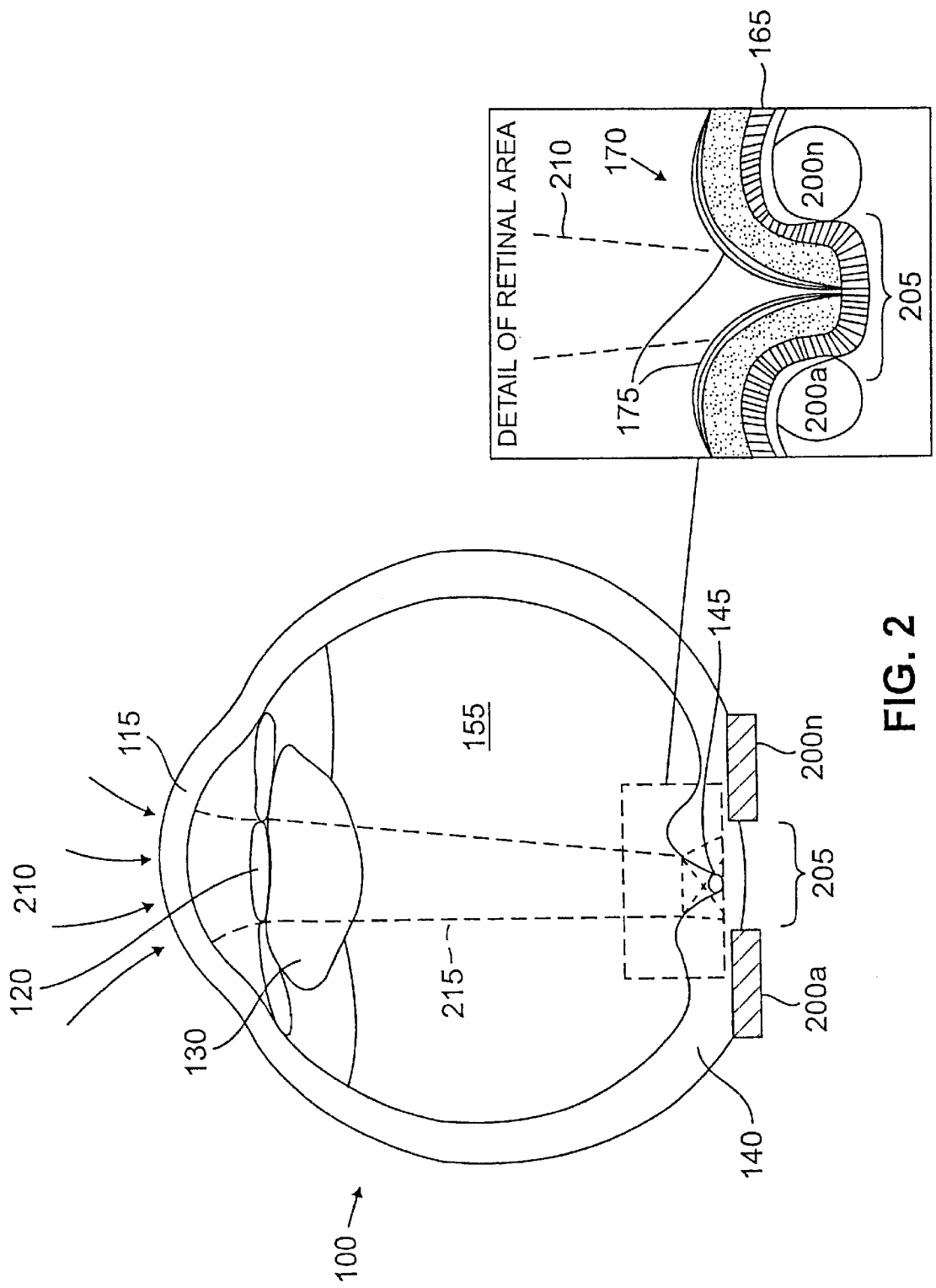
FIG. 2 illustrates a two-dimensional cross-sectional representation of an association of a plurality of segments according to the present invention with an eye for cooperatively treating the effects of macular degeneration.

Turning now to FIG. 2, illustrated is a two-dimensional cross-sectional representation of an, exemplary association of a plurality of segments 200*a* to 200*n* with exemplary eye 100 according to the principles of the present invention for cooperatively treating the effects of macular degeneration. As will be discussed in greater detail hereinbelow, segments 200*a* to 200*n* cooperatively manipulate the retina 140 to augment the photoreceptor cells 165 proximate the macula 145 to form an increased image perception area 205 that preferably encompasses the macula 145.

It should be noted that the prescribed shape of the segments 200 is illustrative only and introduced as a shape adapted to augment the photoreceptor cells 165, and, more particularly, although the bodies of the segments 200 are shown as rectangular, alternate advantageous dimensions and physical shapes may suitably include circular/round (see expansion box), triangular, quadrilateral, conical, or other like physical form, or combination of the same.

Exemplary rays of light 210 pass through the cornea 115 and the pupil 120, intersecting the lens 130, which begins the process of focusing by bending (refracting) the light rays 210. The lens 130 converges the light rays 210 into a beam 215 intercepting the macula 145 and impinging upon the retinal area—the macula 145 represents a focal point for the lens 130. The lens 130 therefore operates to refine the light rays 210 into narrower beams to provide clearer images. Thus, after focusing by the lens 130, the light beam 210 travels through the transparent vitreous humor 155 and impinges the retina 140.

Turning to the expansion box, the retinal area (previously designated 205) contains hundreds of millions of specialized nerve cells arranged in complex patterns. The photoreceptor cells (or "vision receivers") 165 are of two types, namely, rods and cones. The rods outnumber the cones and function best under conditions of low illumination. The cones provide detailed vision and color vision. The heaviest concentration of cone cells in the retina is in the macula 145. The macula 145 includes the fovea 170, an area of extremely sensitive cone cells responsible for discerning fine detail vision. The fovea 170 is damaged as a result of macular degeneration.

Besides the photoreceptor cells 165, the retina 145 includes many other types of connecting and supporting cells within the retinal tissue, such as the retinal pigment epithelium (not shown) which absorbs excess light and provides a nutritive function for the retina 140. More particularly, the clivus 175 is illustrated as "thickenings" of the visual-cell, outer nuclear, inner nuclear, ganglion-cell, and nerve-fiber layers that add up to a local thickening of the retinal area as a whole. An important aspect of the optical properties of the eye is the effect that the varying physical properties of the vitreous humor 155, the retinal tissue, and the photoreceptor cells 165. In short, the vitreous humor 155 is largely transparent, the retinal tissue is, in part, reflective, and the photoreceptor cells 165 are light absorbent.

According to the present embodiment, each segment 200 is, as introduced hereinabove, capable of increasing the depth of the fovea 170 and, in the process, making the sides of the clivus 175 more convex. By increasing the convexity of the sides of the clivus 175, the segments 200a to 200n take advantage of and more fully utilize the varying optical properties of the retinal area, and, in particular, the fovea 170 and the clivus 175, to increase the optical effect of the same. As is illustrated by the retinal area expansion box, the illustrated association of the device segments 200a to 200n with the eye effectively manipulate the retinal area to augment the photoreceptor cells 165 proximate the macula 145.

In short, image beam 215 travels from the lens 130 through the vitreous humor 155 to magnify and impinge a larger image perception area 205 relative to macula 145. The image beam 215 is refracted by the increasingly convex sides of clivus 175 causing the image beam 215 to be spread across a greater number of photoreceptor cells 165. The electrical impulses that are generated by the interaction of the light beam 215 with the photoreceptor cells 165 are transmitted to the optic nerve, which consists of a myriad fibers. The optic nerves from each eye exit the eyeball and join each other at the base of the brain at point called optic chiasm (not shown). At the optic chiasm a complex crossing of nerve fibers occurs and the visual impulses are then passed to the optic tracts which end in the lateral geniculate bodies. From there, visual impulses pass along the optic radiations which terminate in the occipital cortex at the back of the brain. In this area, there are extremely complex interconnections and visual association areas. It is at this point in the process where vision, as we know it, is perceived.

Note that the fovea 170 (in particular, and the retinal tissue, generally) has a relatively higher refractive index than that of the vitreous humor. Therefore, any part of the light beam 215 that strikes the "vitreoretinal" boundary at other than a right angle will refract away from an imaginary perpendicular and "disperse" down to the photoreceptor cells 165. Association of the segments 200 with the eye cooperatively manipulate the retina 140, augmenting the photoreceptor cells 165 proximate the macula 145 to increase the foveal depression to deliberately take advantage of this refraction. The manipulated retinal area causes the formation of an increased image perception area 205; in other words, the foveal portion of the retinal image is expanded on its way through the retinal tissue, and is purposefully magnified when it reaches the level of the photoreceptor cells 165. The increase in the depth of the fovea 170 therefore directly affects visual acuity. In point of fact, the deeper the actual depression proximate the original level of the retina, the higher the mound or 'circumfoveal eminence' created around the depression by the displaced tissue of the clivus 175. The continuous steep slope produced from the crest of the mound to the bottom of the depression becomes an effective magnifying device, of optically unique description.

Again, the segments 200a to 200n, and shapes thereof, are by way of illustration only, and in no means should there use be interpreted as a limitation as to the shape, size, number, or any other physical attributes of the device of the present invention. As will be described below, alternate embodiments of the present invention may suitably include prescribed shapes such as a band, a segment, a partial band, a plate, or, for that matter, any shape suitably adapted to perform the functions described in this patent document, as well as combinations of the same, to treat the effects of eye disorders, such as macular degeneration.

A suitable exemplary procedure for associating the device with the eye might include opening the conjunctiva 110 in the inferior temporal region between the lateral and inferior rectus muscles approximately 6 mm posterior to the limbus. The sclera 105 is cleaned of Tenon's capsule and the dissection is carried posterior to the equator of the eye. A partial thickness scleral incision is made in the sclera 105 to create a scleral pocket that may advantageously extend around or under the macula 145 and the fovea 170, such as the types of scleral pocket disclosed in the Presbyopia and Related Eye Disorder Patent Documents. The device is suitably associated with the eye (such as implanting, suturing, or inserting the same into) via the scleral pocket. The position of the device may be verified by indirect or direct ophthalmoscope. The scleral pocket and the conjunctival incisions are closed with standard ophthalmic sutures. It should be noted that any suitable medical procedure may be undertaken to associate the device with the eye. The relative effectiveness of various procedures may be based, at least in part, upon the size, shape, etc. of the device used.

Figure 3:
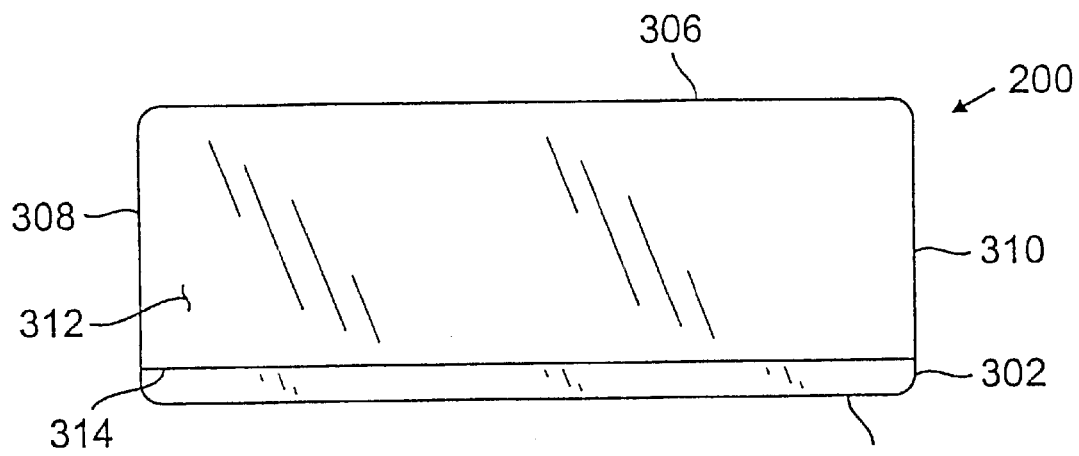
FIG. 3 illustrates a plan view of a segment embodiment of a device according to the principles of the present invention.

Turning to FIG. 3, illustrated is a plan view of a segment embodiment 200 of a device according to the principles of the present invention. For the purposes of illustration, concurrent reference is occasionally made to the exemplary cross-sectional views of the eye of FIGS. 1a, 1b and 2. The exemplary segment body includes a base 302 with an anterior edge 304, a posterior edge 306, and lateral ends 308 and 310, all collectively forming a perimeter for an inner surface 312. The exemplary inner surface 312 includes a ridge 314 illustratively extending along the length of the base 302.

According to this embodiment, the segment 200 may be associated with an eye to increase the depth of the fovea 170 and, in the process, to make the sides of the clivus 175 more convex as described hereinabove, thereby utilizing the varying optical properties of the retinal area 205 to increase the optical effect of the same. In short, a suitable association of this device 200 with the eye 100 will cause an image beam to magnify and impinge an image perception area 205 that is relatively larger than the macula 145.

The exemplary segment body has a prescribed shape, in part due to exemplary ridge 314, that is capable of exert a force on the eye 100, that modifies the shape of the eye 100 to suitably manipulate the retinal area 215 and, possibly, to alter the distance between the lens 130 and the retina 140. Advantageously, the segment body has the inner surface 312 and an outer surface (not shown) that are separated sufficiently, again, in part via exemplary ridge 314, to suitably modify the shape of the eye by exerting the force with respect to the eye 100.

Figure 4:
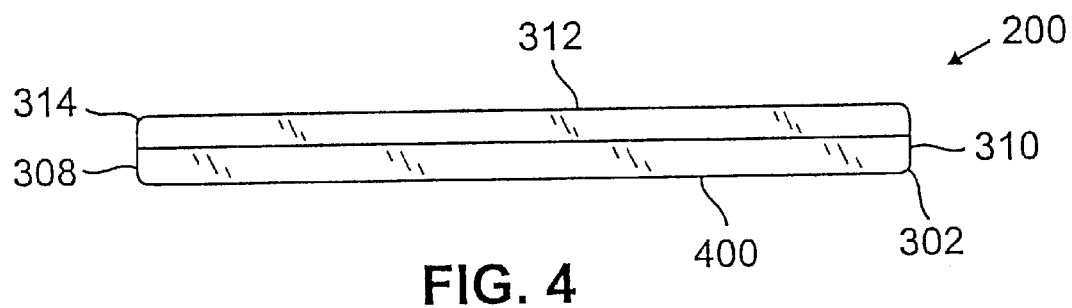
FIG. 4 illustrates a front elevational view of the segment embodiment of FIG. 3.
Figure 5:
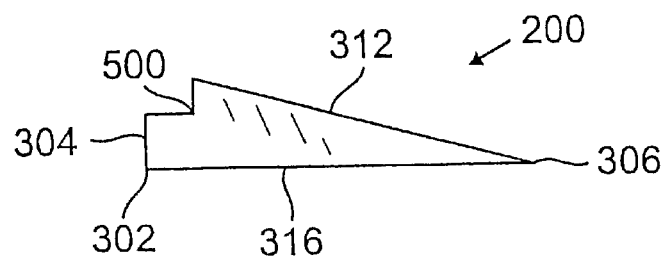
FIG. 5 illustrates a side view of the segment embodiment of FIGS. 3 and 4.

Turning momentarily to FIG. 4, illustrated is a front elevational view of the segment embodiment of FIG. 3. The segment 200 illustrates the base 302, lateral ends 308 and 310, and the ridge 314, along with a flat outer surface 400. Turning next to FIG. 5, illustrated is a side view of the segment embodiment of FIGS. 3 and 4. The segment 200 illustrates the ridge 314, the outer surface 316, and a notch 500 on the inner surface 312 of the device, or prosthesis.

A device in accordance with the principles of the present invention may be made of any suitable material that is sufficiently rigid to exert a force when associated with the eye to manipulate the optical effect of the retinal surface thereof. The device is preferably physiologically acceptable for long-term implantation or contact with the ocular tissues. Such materials are known in the art and include suitable metals (e.g., titanium, gold, platinum, stainless steel, tantalum, various surgically acceptable alloys, etc.), ceramics (e.g., crystalline and vitreous materials such as porcelain, alumina, silica, silicon carbide, high-strength glass, etc.), and synthetic resins (e.g., physiologically inert materials such as polymethyl methacrylate, polyethylene, polypropylene, polytetrafluoroethylene, polycarbonate, silicone resins, etc.). The device may also be made of composite materials incorporating a synthetic resin or other matrix reinforced with fibers of high strength material such as glass fibers, boron fibers or the like (e.g., glass-fiber-reinforced epoxy resin, carbon fiber-reinforced epoxy resin, carbon fiber-reinforced carbon (carbon-carbon), etc.).

In alternate advantageous embodiments, the device may be made from organic materials such as preserved collagen, preserved sclera, and the like, as well as artificial collagen or the like. In other embodiments, the device may be made of a semi-rigid exterior that forms a cavity within the body of the device. The cavity may suitably be empty, or, alternatively, be filled with a liquid, a gel or the like. This embodiment may suitably be alterable so that the dimensions of the same can be altered by injecting various amounts of air, liquid (e.g., water, saline, silicone oil, etc.), or gel (e.g., silicone, collagen, gelatin, etc.). Of course, the semi-rigid exterior may be made of any one or more of the materials set forth or referenced herein. It should be noted that the devices disclosed herein may be associated with micro-electro-mechanical systems ("MEMS") and related technologies to suitably alter or augment one or more of the devices or manipulate use of the same as described herein to increase the optical effect of the retinal surface of the eye.

Figure 6:
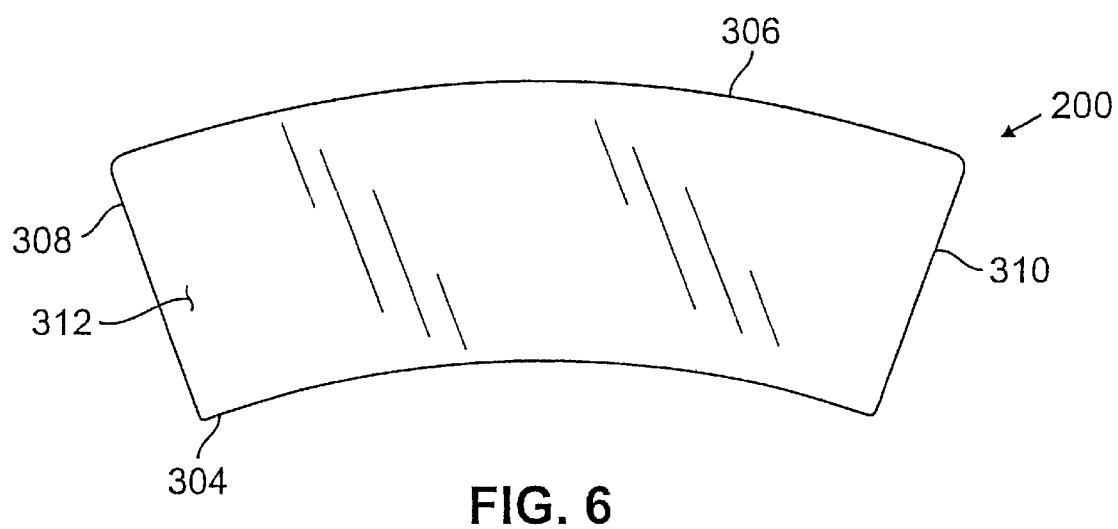
FIG. 6 illustrates a plan view of an exemplary segment embodiment of a device according to the principles of the present invention.

Turning now to FIG. 6, illustrated is a plan view of an exemplary segment embodiment 200 of a device according to the principles of the present invention. For the purposes of illustration, concurrent reference is occasionally made to the exemplary cross-sectional views of the eye of FIGS. 1a, 1b and 2. The exemplary segment body is curved and includes an anterior edge 304, a posterior edge 306, and lateral ends 308 and 310, all collectively forming a perimeter for an inner surface 312. According to this embodiment, the segment 200 may again be associated (alone or in combination with one or more other suitable devices) with an eye to increase the depth of the fovea 170 and, in the process, providing increased convexity to the sides of the clivus 175 to utilize the varying optical properties of the retinal area 205 to increase the optical effect of the same. In short, a suitable association of this device 200 with the eye 100 will cause an image beam to magnify and impinge an image perception area 205 that is relatively larger than the macula 145. The exemplary segment body has a prescribed shape capable of exerting a force to the eye 100 once associated therewith, that modifies the shape of the eye 100 to manipulate the retinal area 215 and, possibly, to alter the distance between the lens 130 and the retina 140. In the present embodiment, the exemplary prescribed shape is curved, and the curvature is chosen to provide at least an approximate match for the curvature of the surface of the eye, or, in alternate embodiments (e.g., FIG. 8), the curvature is chosen to provide at least an approximate match for the curvature of any adjacent device bodies also associated with the eye. As will be described with reference to FIGS. 10 and 11, the segment body has the inner surface 312 and an outer surface (not shown) that are separated sufficiently to suitably modify the shape of the eye by exerting the force with respect thereto.

Figure 7:
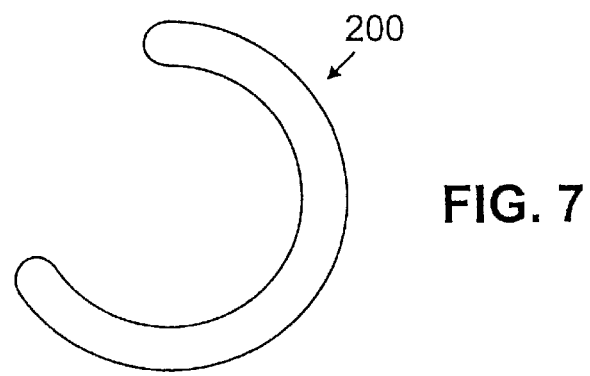
FIG. 7 illustrates a plan view of an exemplary partial band embodiment of a device according to the principles of the present invention.
Figure 8:
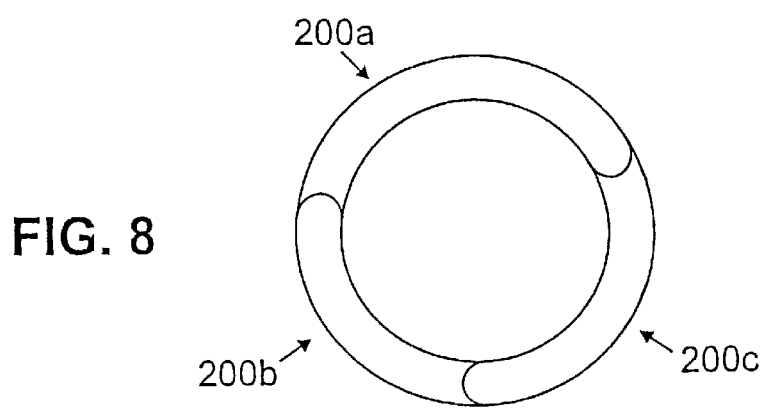
FIG. 8 illustrates a plan view of a plurality of associated segments that cooperate to form a band embodiment of a device according to the principles of the present invention.
Figure 9:
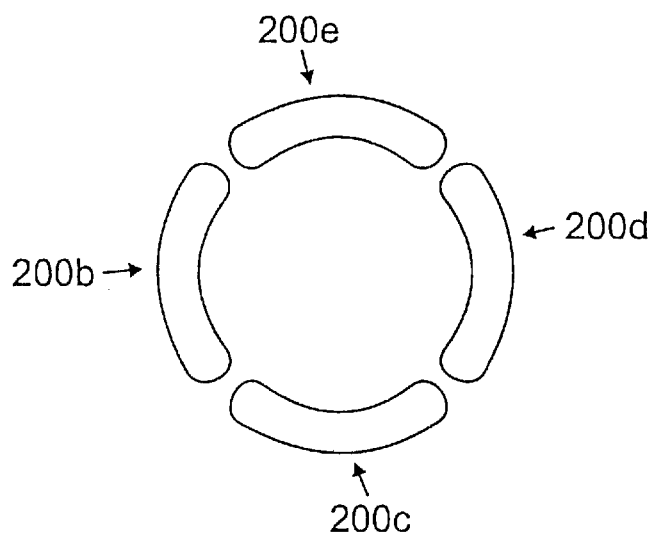
FIG. 9 illustrates a plan view of a plurality of disassociated segments that cooperate to form a band embodiment of a device according to the principles of the present invention.

Turning momentarily to FIG. 7, illustrated is a plan view of an exemplary partial band embodiment 200 of a device according to the principles of the present invention. The partial band, when suitably associated with an eye, has a shape prescribed to increase the depth of the fovea 170 and to provide increased convexity to the sides of the clivus 175. Again, this utilizes the varying optical properties of the retinal area to increase the optical effect of the same. In short, the partial band will cause an image beam traveling from the lens of the eye through the vitreous humor to magnify and impinge an image perception area 205 that is relatively larger than the macula. Similarly, FIG. 8 illustrates a plan view of a plurality of associated segments 200a to 200d that cooperate to form a complete band, or "donut," embodiment 200 of a device according to the principles of the present invention. In contrast, FIG. 9 illustrates a plan view of a plurality of disassociated segments 200a to 200d that cooperate to form an implicit band embodiment 200 of a device according to the principles of the present invention.

It will also be understood by the skilled practitioner that any of the devices described herein, as well as equivalent constructions within the spirit and scope of the present invention in its broadest form, may suitably be associated with the eye, and, in particular, the retinal area, surgically through a scleral pocket, or belt loop, sutured, stapled, bonded, or otherwise physically associated with the eye to manipulate the retinal area in accordance with the teachings or referenced herein. It should also be understood that the material of which any of the foregoing devices, or, for that matter, any device in accord with the teachings hereof, is made may be adapted to any suitable particular shape or design chosen therefor.

Figure 10:
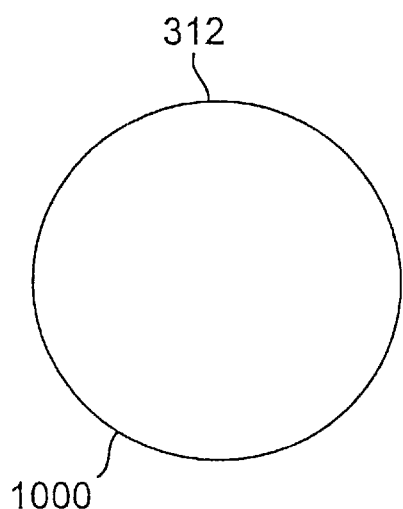
FIG. 10 illustrates a round/circular shaped body of a device having a solid core.
Figure 11:
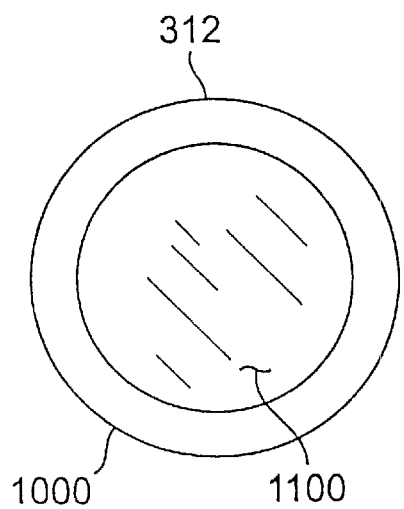
FIG. 11 illustrates a round/circular shaped body of a device having a liquid/gel filled cavity.

For instance, FIGS. 10 and 11 illustrate a round/circular shaped body of device 200 respectively having a solid core and a liquid/gel filled cavity 1100. In both illustrations, the device body has a top surface 312 and a bottom surface 1000 that are separated sufficiently to suitably modify the shape of the eye by exerting the force with respect thereto. The filled cavity 1100 may suitably be filled with a liquid, a gel or the like to alter dimensions of the device.

Regardless, the devices of the present invention may be manufactured by any conventional or later developed technique appropriate to the material used, such as machining, injection molding, heat molding, compression molding and the like. Similarly, the devices hereof may be foldable, made in a plurality of segments, or otherwise manufactured so that it can be assembled prior to use or may be installed separately to form a complete device.

Although the principles of the present invention have been described in detail, those of ordinary skill in the art should understand that they can make various changes, substitutions and alterations herein without departing from the spirit and scope of the invention in its broadest form. For instance, although use of the devices of the present invention have been described with reference to treatment of macular degeneration and other like eye disorders in humans, this treatment may also be applicable to treating various eye disorders suffered by other animals. It should be noted that the Presbyopia and Related Eye Disorder Patent Documents include descriptions of devices directed to the treatment of presbyopia and other like eye disorders.

What is claimed is:

1. A device to treat the effects of macular degeneration comprising a body having a prescribed shape of at least a partial band that is adapted for association with an eye to manipulate the retina of the eye to effectively augment the photoreceptor cells proximate the macula of the eye.

2. The device as set forth in claim 1 wherein said prescribed shape of said body of said device is capable, when associated with the eye, of altering the optical effect of the clivus.

3. The device as set forth in claim 1 wherein said prescribed shape of said body of said device is capable of manipulating the retina of the eye to alter the depth of the fovea.

4. The device as set forth in claim 1 wherein said prescribed shape of said body of said device is capable of manipulating the retina of the eye to alter the convexity of the clivus, effectively augmenting the photoreceptor cells proximate the macula the eye, thereby forming an increased image perception area encompassing the macula to treat the effects of macular degeneration.

5. The device as set forth in claim 1 wherein said body of said device has at least two surfaces that are sufficiently separated to exert a force with respect to the eye.

6. The device as set forth in claim 1 wherein said prescribed shape of said body of said device exerts said force inwardly with respect to the eye.

7. A device to treat the effects of macular degeneration comprising a body having a prescribed shape of at least a segment that is adapted for association with an eye to manipulate the retina of the eye to effectively augment the photoreceptor cells proximate the macula of the eye.

8. The device as set forth in claim 7 wherein said prescribed shape of said body of said device is capable, when associated with the eye, of altering the optical effect of the clivus.

9. The device as set forth in claim 7 wherein said prescribed shape of said body of said device is capable of manipulating the retina of the eye to alter the depth of the fovea.

10. The device as set forth in claim 7 wherein said prescribed shape of said body of said device is capable of manipulating the retina of the eye to alter the convexity of the clivus, effectively augmenting the photoreceptor cells proximate the macula the eye, thereby forming an increased image perception area encompassing the macula to treat the effects of macular degeneration.

11. The device as set forth in claim 7 wherein said body of said device has at least two surfaces that are sufficiently separated to exert a force with respect to the eye.

12. The device as set forth in claim 7 wherein said prescribed shape of said body of said device exerts said force inwardly with respect to the eye.

13. A device to treat the effects of macular degeneration comprising a body having a prescribed shape of a plate that is adapted for association with an eye to manipulate the retina of the eye to effectively augment the photoreceptor cells proximate the macula of the eye.

14. The device as set forth in claim 13 wherein said prescribed shape of said body of said device is capable, when associated with the eye, of altering the optical effect of the clivus.

15. The device as set forth in claim 13 wherein said prescribed shape of said body of said device is capable of manipulating the retina of the eye to alter the depth of the fovea.

16. The device as set forth in claim 13 wherein said prescribed shape of said body of said device is capable of manipulating the retina of the eye to alter the convexity of the clivus, effectively augmenting the photoreceptor cells proximate the macula the eye, thereby forming an increased image perception area encompassing the macula to treat the effects of macular degeneration.

17. The device as set forth in claim 13 wherein said body of said device has at least two surfaces that are sufficiently separated to exert a force with respect to the eye.

18. The device as set forth in claim 13 wherein said prescribed shape of said body of said device exerts said force inwardly with respect to the eye.

* * * * *